(12) United States Patent
Eggert et al.

(10) Patent No.: US 8,261,443 B2
(45) Date of Patent: Sep. 11, 2012

(54) UNDERFILLING OF PRE-MOLDED COMPONENTS

(75) Inventors: Joel T. Eggert, Champlin, MN (US); Joseph A. Cihlar, East Bethel, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 464 days.

(21) Appl. No.: 12/611,338

(22) Filed: Nov. 3, 2009

(65) Prior Publication Data

US 2010/0115770 A1    May 13, 2010

Related U.S. Application Data

(60) Provisional application No. 61/113,838, filed on Nov. 12, 2008.

(51) Int. Cl.
   *H01R 43/02* (2006.01)
(52) U.S. Cl. .......... 29/877; 29/874; 29/876; 29/883
(58) Field of Classification Search ............ 29/877, 29/874, 876, 883; 439/585, 669, 736, 874, 439/877; 607/113, 115, 120, 122
See application file for complete search history.

(56) References Cited

U.S. PATENT DOCUMENTS

| 4,572,602 A * | 2/1986 | Rupnik .......... 439/350 |
| 4,572,605 A | 2/1986 | Hess |
| 5,720,631 A | 2/1998 | Carson et al. |
| 5,999,858 A | 12/1999 | Sommer et al. |
| 6,221,024 B1 | 4/2001 | Miesel |
| 6,501,990 B1 | 12/2002 | Sundberg et al. |
| 7,363,091 B1 * | 4/2008 | Chen et al. ........ 607/120 |
| 2007/0202728 A1 | 8/2007 | Olson et al. |
| 2008/0139053 A1 | 6/2008 | Ries et al. |

FOREIGN PATENT DOCUMENTS

| EP | 0518364 A2 | 12/1992 |
| EP | 0617978 A2 | 10/1994 |
| WO | 2009045772 A1 | 4/2009 |

OTHER PUBLICATIONS

International Search Report and Written Opinion issued in PCT/US2009/063122, mailed Mar. 9, 2010, 13 pages.

* cited by examiner

*Primary Examiner* — Thiem Phan
(74) *Attorney, Agent, or Firm* — Faegre Baker Daniels LLP (57) ABSTRACT

During assembly of a medical electrical lead, the tubular lead component is slid over the outer surface of the lead body to a desired location on the lead. The ends of the tubular lead body are sealed and a space is defined between the inner surface of the tubular lead component and the outer surface of the lead body. Medical adhesive is injected through the port(s) to substantially fill the space between the tubular component and the lead body. The adhesive is then cured. Any ports extending away from the sleeve are removed after the curing step.

16 Claims, 8 Drawing Sheets

UNDERFILLING OF PRE-MOLDED COMPONENTS

CROSS-REFERENCE TO RELATED APPLICATION

This application claims the benefit under 35 U.S.C §119 of U.S. Provisional Application No. 61/113,838, filed on Nov. 12, 2008, entitled "UNDERFILLING OF PRE-MOLDED COMPONENTS," which is herein incorporated by reference in its entirety.

TECHNICAL FIELD

The present invention relates to medical electrical leads and methods of assembling a medical electrical lead. More particularly, the present invention relates to a method of attaching a pre-molded, tubular lead component onto a medical electrical lead body.

BACKGROUND

Medical electrical leads generally include one or more tubular components secured to the body of the lead. Such tubular lead components are typically secured to the lead body by manually injecting medical adhesive into one end of the tubular lead component until the adhesive exits from the opposite end. The adhesive is then cured to secure the lead component onto the lead body. Injecting medical adhesive in this manner may be imprecise, may cause excess adhesive to leak outside of the tubular component, and may be prone to low reproducibility. Additionally, manually injecting medical adhesive does not ensure that the medical adhesive is uniformally distributed around the circumference of the lead body for maximum bonding capabilities.

SUMMARY

In one embodiment, the present invention is a method of assembling a medical electrical lead having a lead body with an outer surface including a proximal end, a distal end, and at least one conductor extending from the proximal to the distal end and an outer surface. A tubular lead component including a first end, a second end and a lumen with an inner surface, is assembled onto the lead body by sliding the tubular lead component over an outer surface of the lead body to a desired location. A space is defined between the outer surface of the lead body and the inner surface of the tubular lead component. The tubular component includes at least a first port and at least a second port, which extend into the space defined between the outer surface of the lead body and the inner surface of the tubular component. One or more of the ports may include a neck extending away from the tubular lead component and a bore extending within the neck through the sleeve into the space defined between the lead body and the tubular lead component. After the tubular lead component has been assembled onto the lead, the first and second ends of the tubular lead component are circumferentially sealed. Then, medical adhesive is injected through at least one port to substantially fill the space defined between the tubular lead component and the lead body. Next, the adhesive is cured to secure the tubular lead component onto the lead body. Extended portions of the ports may be removed after the adhesive has been cured.

In another embodiment, the present invention is a method of assembling a medical electrical lead, in which a tubular lead component is positioned onto a lead body having an outer surface. The tubular lead comprises a sleeve including a first end and a second end and lumen having an inner surface extending between the first and second ends. A space is defined between the outer surface of the lead body and the inner surface of the tubular lead component. The tubular lead component further includes at least a one fill port and at least one vent port located on the sleeve. After the tubular lead component has been positioned onto the lead body, a sealing device with a circular cross-section is applied to the first and second ends of the tubular lead component to circumferentially seal the first and second ends. Next, a medical adhesive is delivered through the fill port to substantially fill the space defined between the outer surface of the lead body and the inner surface of the tubular component. The medical adhesive is then cured to secure the tubular component to the lead body. After the medical adhesive has been cured, extended portions of the ports are then removed.

In another embodiment, the present invention is a medical electrical lead including one or more tubular lead components assembled according to any of the methods described above.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIGS. 1A-1D are isometric views of a tubular lead component 10 according to various embodiments of the present invention. In general, each of the tubular lead components include a tubular sleeve 12 including a lumen 14 and one or more ports 24. According to some embodiments of the present invention, as shown in FIGS. 1A-1D, the ports 24 include a neck portion 26 extending away from the sleeve 12. Each of the tubular lead components 10 is configured to slide over and be secured to an outer surface of a medical electrical lead body during assembly of the lead. Exemplary tubular lead components 10 include, but are not limited to, terminal boots, front terminal seals, rear terminal seals, distal tip necks, tined distal tip necks, inner insulators, and other tubular lead body components known to those of skill in the art.

Figure 1A:
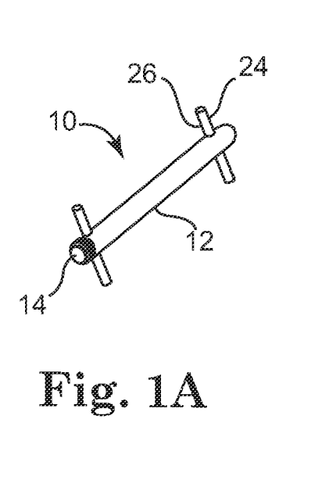
FIGS. 1A-1D are isometric views of tubular lead components provided in accordance with various embodiments of the present invention.
Figure 1B:
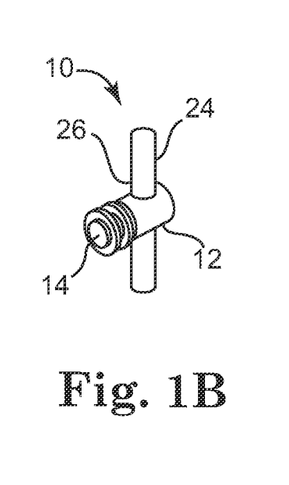
Figure 1C:
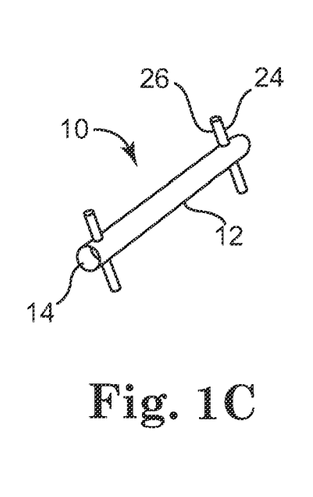
Figure 1D:
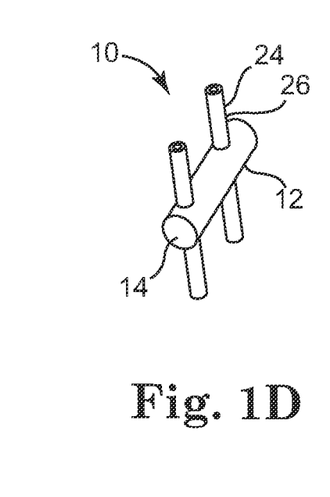
Figure 2A:
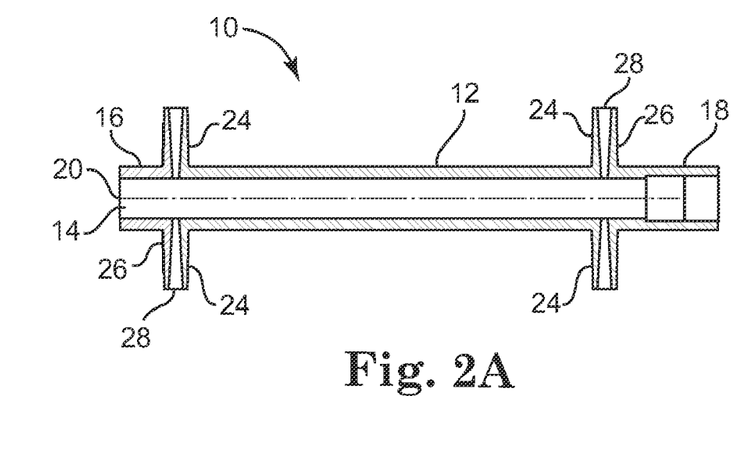
FIGS. 2A-2E are longitudinal cross-sectional views of tubular lead components provided in accordance with various embodiments of the present invention.
Figure 2B:
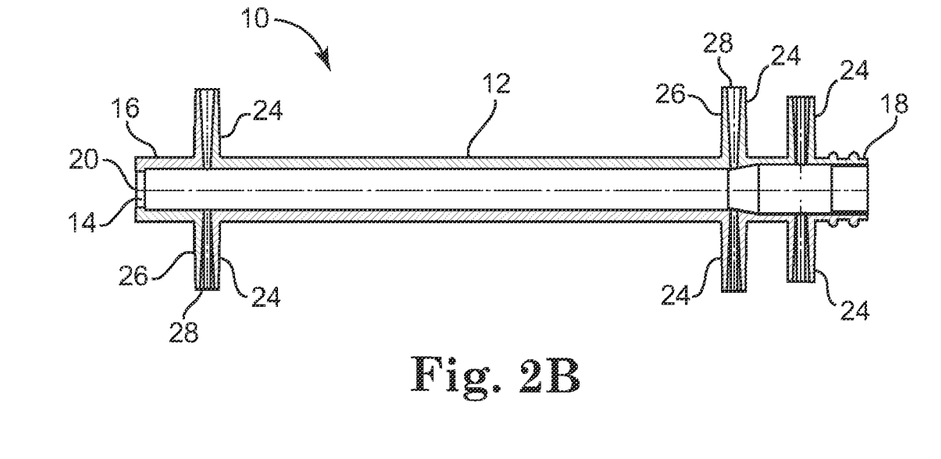
Figure 2C:
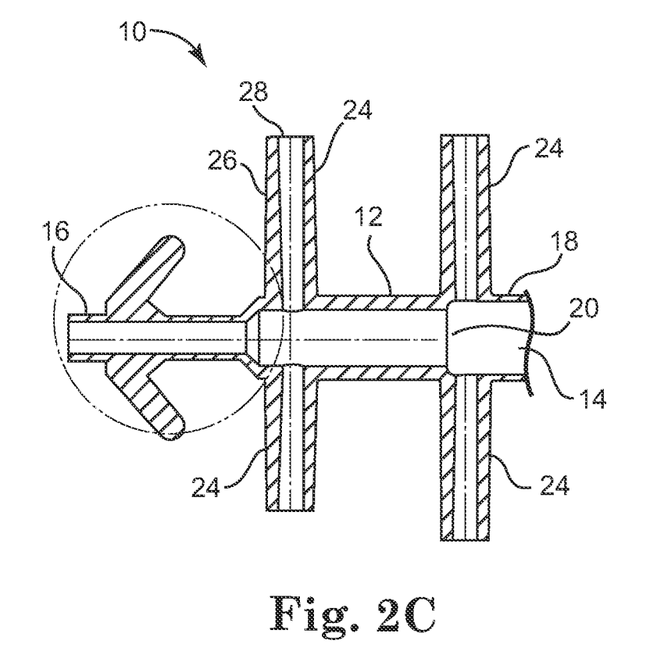
Figure 2D:
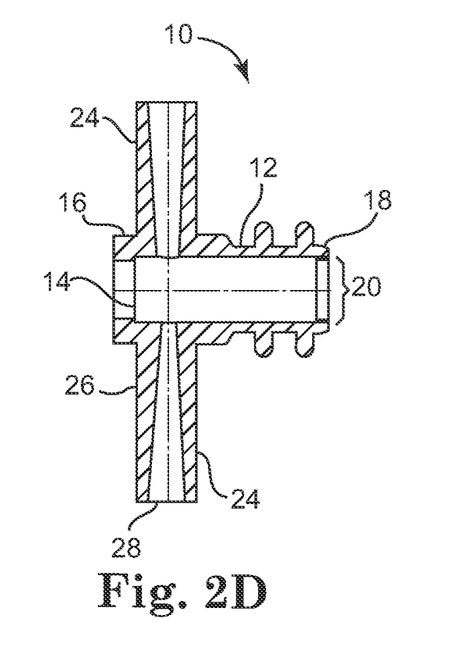
Figure 2E:
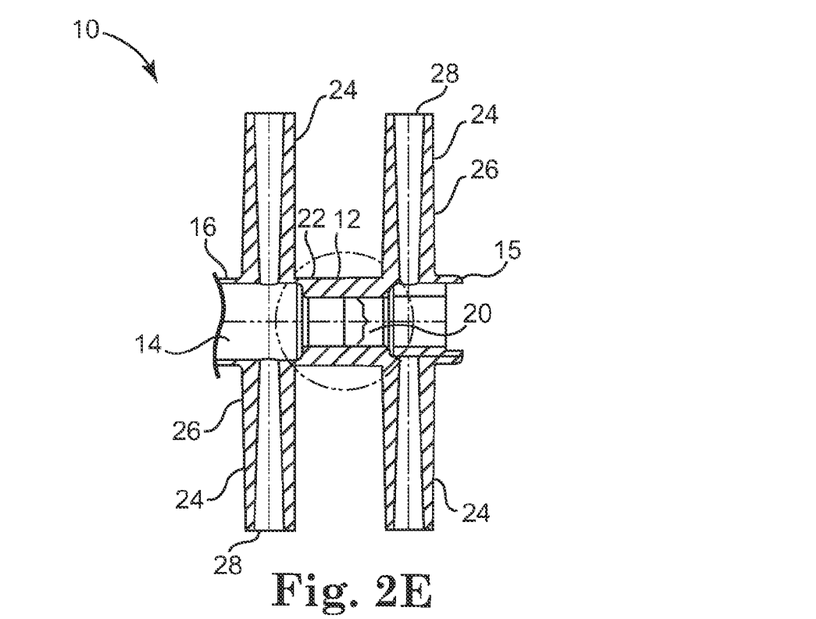

FIGS. 2A-2E are longitudinal cross-sectional views of a tubular lead component 10 according to various embodiments of the present invention, which includes a sleeve 12 having a lumen 14 extending between a proximal end 16 and a distal end 18. In some embodiments, an inner diameter 20 of the lumen 14 varies along the length of the sleeve 12. For example, as best shown in FIG. 2E, the sleeve 12 includes a lumen 14 having a smaller inner diameter 20 in a middle portion 22 of the sleeve 12. This may be advantageous when fitting the tubular lead component 10 onto a lead body, as the smaller inner diameter lumen 20 creates a snug fit between the lead body and the tubular lead component 10.

According to various embodiments, the tubular lead component 10 includes at least two ports 24. The port(s) 24 can serve as either a fill port or a vent port and are generally interchangeable. The port(s) 24 can be positioned at various locations along the sleeve 12. In certain embodiments, as shown in FIGS. 2A-2E, a first port 24 is located on the sleeve 180° opposite a second port 24. In other embodiments, the ports 24 can be located on the same side of the sleeve. In some embodiments, as best shown in FIG. 2A, the ports 24 are located at opposite ends of the sleeve 12. In other embodiments, as best shown in FIG. 2B, the ports 24 are located on the sleeve 12 in close proximity to one another.

Figure 3A:
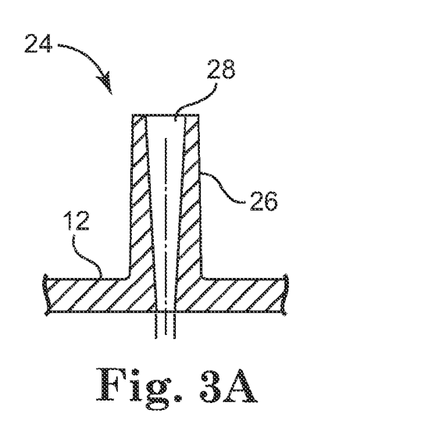
FIGS. 3A and 3B are longitudinal, cross-sectional views of tubular lead component ports according to embodiments of the present invention.
Figure 3B:
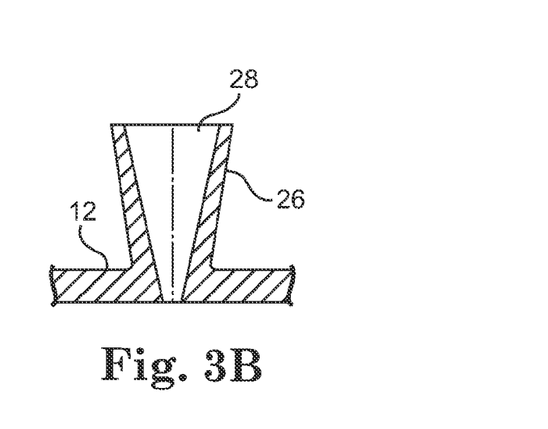

According to various embodiments, the port(s) 24 include a neck 26 extending away from the sleeve 12 and a bore 28 extending within the neck 26 through the sleeve 12 and into the lumen 14. FIGS. 3A and 3B are close-up longitudinal cross-sectional views of a port 24 including a neck 26 having a bore 28. The neck 26 has a cylindrical or frustoconical shape. Additionally, in certain embodiments, the bore 28 also is cylindrical or frustoconical in shape. The shape of the bore 28 can be independent of the shape of the neck 26. In one embodiment, the bore 28 is frustoconically shaped and is configured to mate with an injection needle. When mated with the injection needle, the bore 28 becomes sealed and serves as a gasket for injection. In other embodiments of the present invention, the port(s) 24 do not include a neck and simply include a bore formed in the sleeve 12 extending into the lumen 14.

Figure 4A:
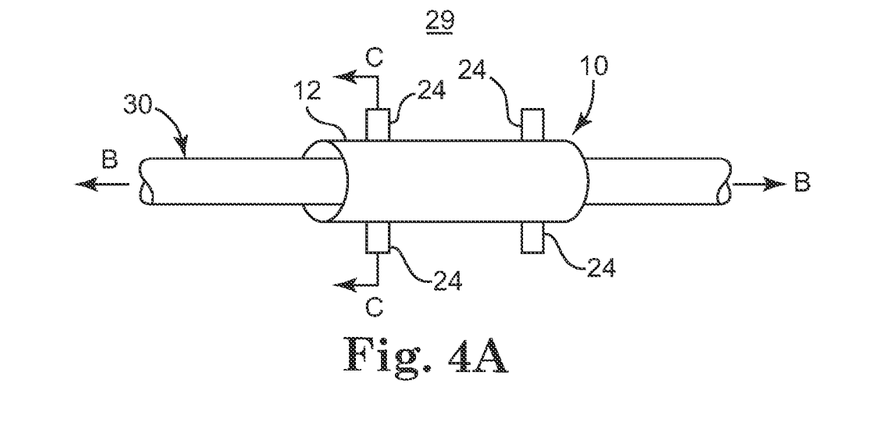
FIG. 4A is a schematic view of a tubular lead component secured to a lead body according to an embodiment of the present invention.
Figure 4B:
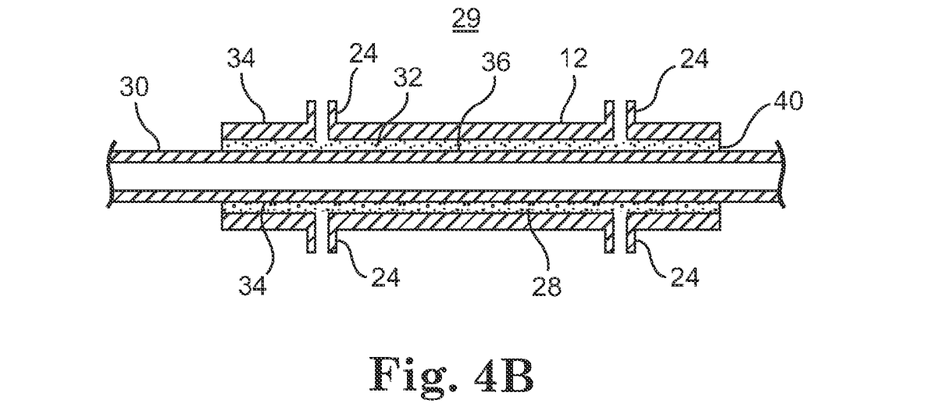
FIG. 4B is a longitudinal cross-sectional view of the tubular lead component and lead body shown in FIG. 4A.
Figure 4C:
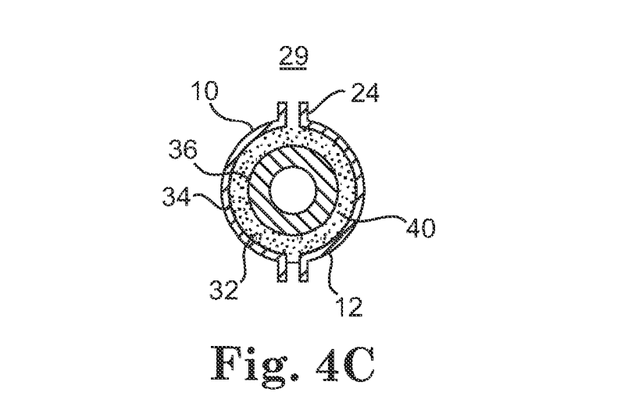
FIG. 4C is an end cross-sectional view of the tubular lead component and lead body shown in FIG. 4A.

FIG. 4A is a schematic view of a lead assembly 29 including a tubular lead component 10 secured to a portion of a lead body 30. FIG. 4B is a longitudinal cross-sectional view of the tubular lead component 10 and the lead body 30 taken along the lines B-B. FIG. 4C is an end cross-sectional view of the tubular lead component 10 secured to the lead body 30 taken along the line C-C shown in FIG. 4A. As best shown in FIGS. 4B and 4C, a space 32 is defined between an inner surface 34 of the tubular lead component 10 and an outer surface 36 of the lead body 30. In certain embodiments, the space 32 is an annular space, circumferentially surrounding the outer surface 36 of the lead body 30.

According to some embodiments, as best shown in FIGS. 4A and 4B, the tubular lead component 10 can include two sets of ports 24. Each set of ports 24 includes a first port 24 located opposite a second port 24 on the sleeve 12. At least one port 24 serves as a fill port and at least one port 24 serves as a vent port. Medical adhesive 40 is injected through at least one port 24 into the space 32 defined between the tubular component 10 and the lead body 30. Exemplary medical adhesives include, but are not limited to, the following: silicone adhesives, epoxy based adhesives, Rehau 1511, and other medical adhesives known to those of skill in the art. In some embodiments, the medical adhesive 40 is injected through at least one port 24 until at least some of the medical adhesive 40 exits through one or more vent ports 24 provided on the tubular component 10. In other embodiments a predetermined amount of medical adhesive 40 is injected through at least one of the fill ports 24.

Figure 5:
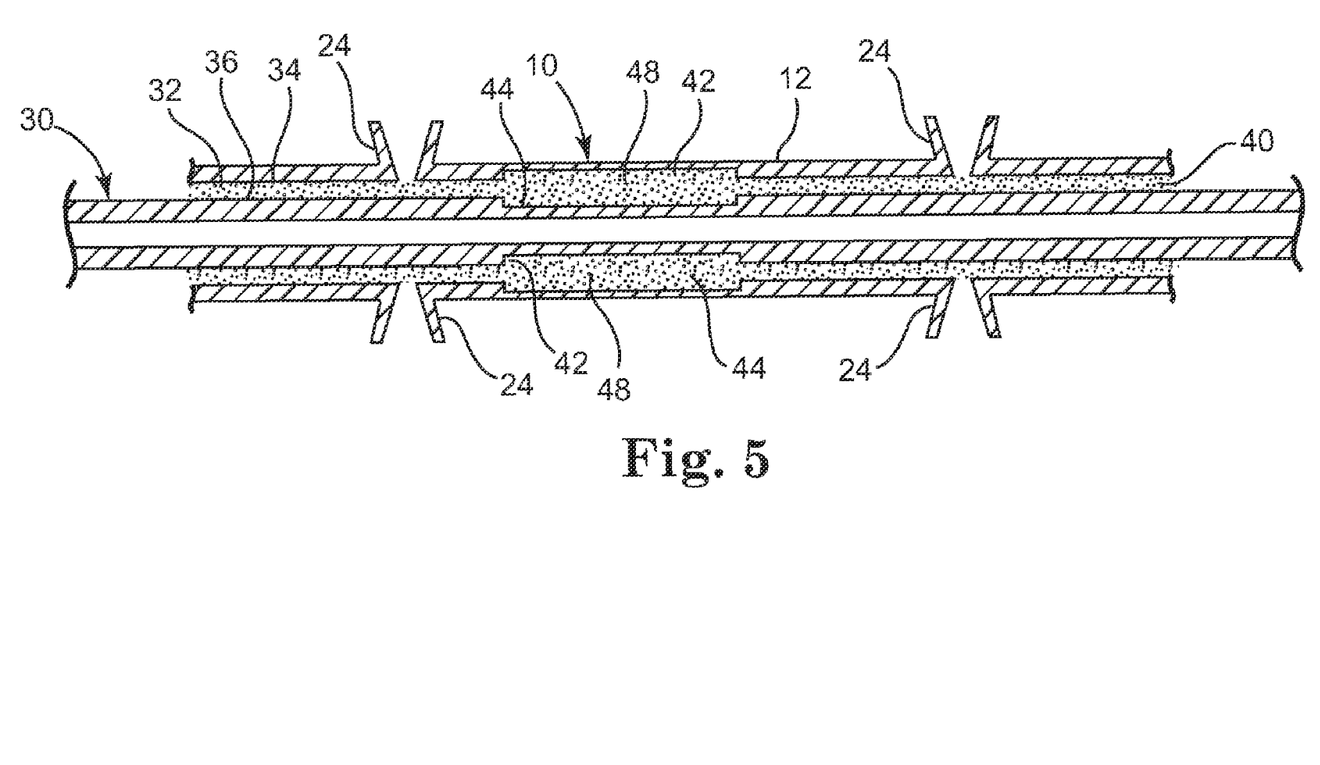
FIG. 5 is a longitudinal cross-sectional view of a tubular lead component secured to a lead body according to another embodiment of the present invention.

FIG. 5 is a longitudinal cross-sectional view of a tubular lead component 10 secured to a lead body 30 according to another embodiment of the present invention. As shown in FIG. 5, the tubular lead component 10 includes at least a first groove 42 formed in the inner surface 34 of the component 10. In some embodiments, the outer surface of the lead body 30 can also include a groove 44. The grooves 42, 44 can be configured to control and direct the flow of medical adhesive 40 into the space 32 defined between the lead body 30 and the tubular lead component 10. According to a further embodiment, as shown in FIG. 5, the first and second grooves 42, 44 are configured to mate together such that they define a channel 48. When adhesive 40 is injected through the one or more ports, the channel 48 defined by the grooves 42, 44 controls and directs the flow of adhesive into the space.

Figure 6:
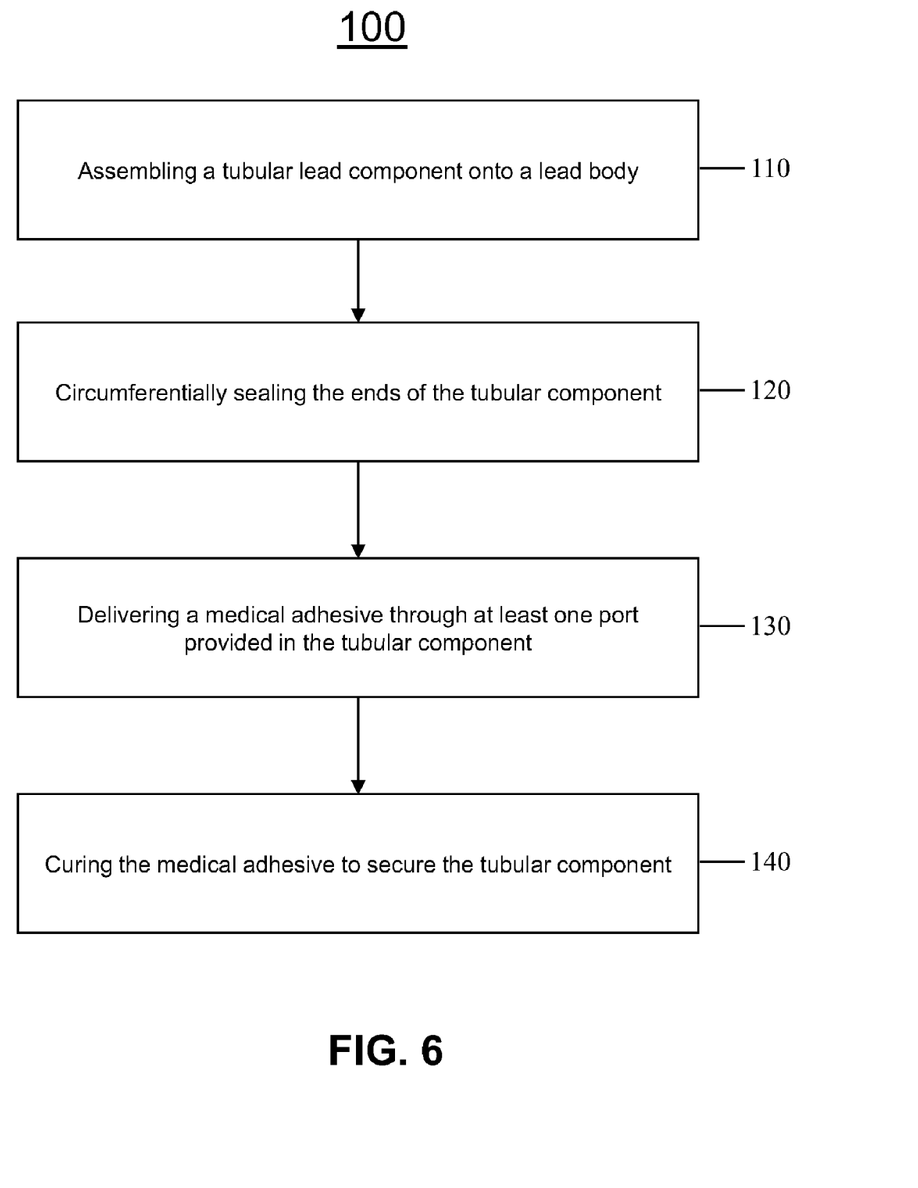
FIG. 6 is a flow chart of a method according to one embodiment of the invention.

FIG. 6 is a flow chart of a method 100 according to one embodiment of the invention. First, a tubular lead component, such as any one those described above, is slid over the outer surface of a lead body to a desired location on the lead body (Block 110). Next, the first and second ends of the tubular lead component are circumferentially sealed such that a space is defined between the inner surface of the lead body component and the outer surface of the lead body (Block 120). A medical adhesive is then injected through one or more ports until the space between the tubular component and the lead body is substantially filled (Block 130). In some embodiments, the medical adhesive is injected through the ports until at least a portion of the medical adhesive begins to exit one or more vent ports. In other embodiments, a predetermined amount of medical adhesive is injected through one or more ports.

The adhesive is then cured to secure the tubular component to the lead body (Block 140). In some embodiments, the adhesive is cured by placing the lead assembly into an oven at an appropriate temperature for curing the adhesive. In other embodiments, the lead assembly may be left at room temperature for a sufficient amount of time for curing to occur. After the curing step, any ports extending away from the tubular lead component are then removed. In some embodiments, the ports may be die cut from the tubular lead component. One or more witness marks may be present indicating the location of the ports on the sleeve of the tubular component.

Any sealing device having circular cross-section and capable of forming a seal around a lead assembly can be used to circumferentially seal the first and second ends of the tubular lead component during assembly of the lead. A circumferential seal is formed by applying a circumferential pressure to the first and second ends of the tubular lead component such that the inner surface of the lead component contacts the outer surface of the lead body around a circumference of the lead body. The first and second ends should be sufficiently sealed so as to prevent any potential leakage of medical adhesive during assembly of the lead body. Sealing both ends of the tubular component on the lead body prevents leakage of the medial adhesive during injection, making the process clean and efficient.

Figure 7A:
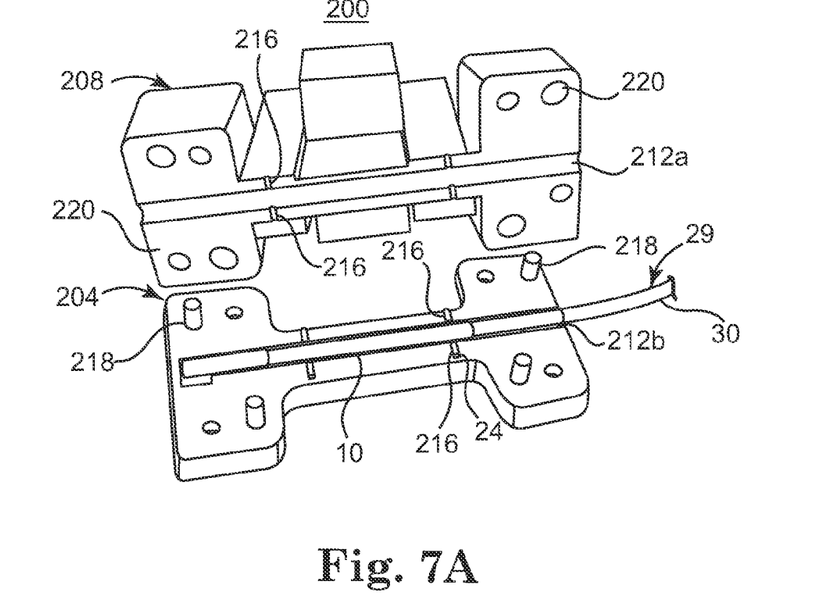
FIG. 7A is a schematic view of a sealing device provided in accordance with one embodiment of the present invention.

FIG. 7A is a schematic view of an exemplary sealing device 200 used to circumferentially seal the first and second ends of the tubular lead component according to one embodiment of the present invention. The sealing device 200 includes a first plate 204 and a second plate 208. The first and second plates 204 and 208 are mirror images of one another and are configured to mate together in an opposing relationship. Each plate 204 and 208 includes a major channel 212a, 212b (represented by dashed lines) having a semi-circular cross-section and dimensions generally corresponding to the outer dimensions of a tubular lead component 10 assembled onto a lead body 30. The dimensions of the major channels 212a, 212b can be selected such that they limit the expansion of the tubular lead component to a pre-determined maximum diameter, thereby preventing over-expansion of the tubular lead component during injection of the medical adhesive. Additionally, each plate 204, 208 also includes one or more minor channels 216 having a semi-circular cross-section and dimensions generally corresponding to the dimensions of any ports 24 located on the tubular lead component 10. In some embodiments, the first plate 204 includes one or more screws 218 or other suitable fastening means known to those of skill in the art and the second plate includes one or more holes 220 configured to receive the screws 218.

Figure 7B:
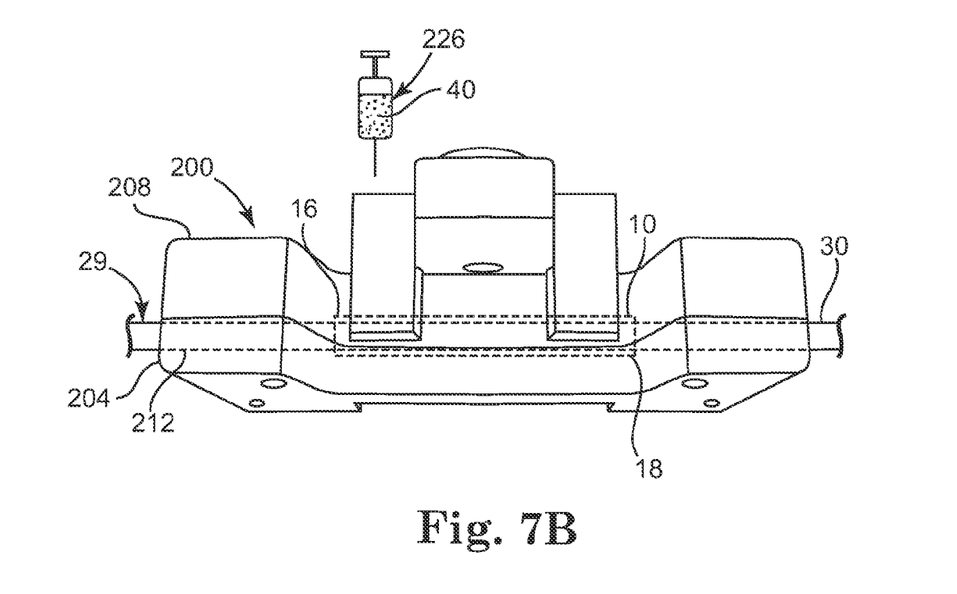
FIG. 7B is a schematic view of the device of FIG. 7A in use.

FIG. 7B is a schematic view of the sealing device 200 in use. A lead assembly 29 including a tubular lead component 10 assembled onto a lead body 30 is placed into the main channel 212 of the first or second plate 204 or 208 such that at least one port 24 is aligned with one of the minor channels 216 provided in the plates 204, 208. In embodiments of the present invention where the tubular lead component 10 includes two or more ports, at least two ports 24 should be aligned with one of the minor channels 216. The two plates 204 and 208 are then fit together in an opposing relationship such that the major channels 212a, 212b in each of the plates 204, 208 form a channel 212 having a circular cross-section. Additionally, when the two plates 204, 208 are placed together as shown in FIG. 7B, the minor channels 216 fit together to facilitate access to the one or more ports 24 located on the tubular lead component 10 utilized for injection of the medical adhesive. Additionally, the minor channels 216 also facilitate the exit of the adhesive from the lead body assembly via one or more vent ports 24.

When the two plates are fit together, dowel pins 218 or other fastening means (e.g. screws) are tightened to circumferentially seal the first and second ends 16, 18 of the tubular lead component 10 about the lead body 30. Alternatively, one or more external clamps may be applied to the plates 204, 208 to apply an external pressure to seal the first and second ends 16, 18 of the tubular lead component 10. Medical adhesive 40 is then injected through at least one port 24 into the space defined between the tubular component 30 and the lead body 30 via a syringe 226 or other injection means known to those of skill in the art. The adhesive is then cured to secure the tubular component to the lead body. The lead assembly 29 is then removed from the sealing device 200. In some embodiments, the adhesive is cured by placing the lead assembly into an oven at an appropriate temperature for curing the adhesive. In other embodiments, the lead assembly may be left at room temperature for a sufficient amount of time for curing to occur. After the tubular component has been secured to the lead body 30, the ports 24 can be removed. These steps can be repeated as necessary to secure additional tubular lead components onto the lead body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of assembling a lead body comprising:
providing a lead body having a proximal end, a distal end, and an outer surface;
positioning a tubular lead component onto the lead body, the tubular lead component comprising a sleeve including a first end and a second end, a lumen having an inner surface extending between the first and second ends, and at least a first port and a second port located on the sleeve, wherein a space is defined between the outer surface of the lead body and the inner surface of the tubular lead component;
circumferentially sealing the first end and the second end of the tubular component to the outer surface of the lead body;
delivering a medical adhesive through the first port to substantially fill the space defined between the outer surface of the lead body and the inner surface of the tubular component; and
curing the medical adhesive to secure the tubular component.

2. The method according to claim 1, wherein a portion of the first or second port extends away from an outer surface of the sleeve.

3. The method according to claim 2, further comprising the step of removing the extending portion.

4. The method according to claim 1, wherein the step of filling the space comprises injecting a predetermined amount of the medical adhesive through the first port into the space defined between the inner surface of the tubular lead component and the outer surface of the lead body.

5. The method according to claim 1, further comprising delivering medical adhesive through the first port with the medical adhesive until a small amount exits through the second port.

6. The method according to claim 1, further comprising providing at least a first groove in the outer surface of the lead body and a second groove in the inner surface of the tubular component, the first and second grooves defining a channel and configured to direct and to control a flow of the medical adhesive.

7. The method according to claim 1, wherein the tubular lead component comprises a sleeve and the first port comprises a neck extending away from the sleeve and a bore extending through the sleeve into the space defined between the inner surface of the tubular lead component and the outer surface of the lead body.

8. The method according to claim 7, wherein the bore comprises a frustoconical shape.

9. The method according to claim 1, wherein the tubular lead component is any one of a terminal boot, a front terminal seal, rear terminal seal, distal tip neck, a tined distal tip neck or an inner insulator.

10. The method according to claim 1, wherein the medical adhesive is any one of a medical epoxy, a silicone adhesive, or Rehau 1511.

11. The method according to claim 1, wherein the sealing step comprises applying a sealing device having a circular cross-section to the first and second ends of the tubular lead component to circumferentially seal the first and second ends.

12. The method according to claim 11, further comprising removing the sealing device from the first and second ends.

13. The method according to claim 11, wherein the sealing device comprises a channel having dimensions generally corresponding to an outer dimension of the tubular lead component.

14. The method according to claim 11, wherein the sealing device comprises ports configured to be aligned with the first and second ports located on the tubular lead component.

15. The method according to claim 1, wherein the first port and the second port are on a common side of the tubular lead component.

16. The method according to claim 1, wherein the first port and the second port are radially spaced apart such that the first port is on a side of the tubular lead component opposite that of the second port.

* * * * *